(12) United States Patent
Hanley

(10) Patent No.: US 6,869,421 B2
(45) Date of Patent: Mar. 22, 2005

(54) DEVICE FOR NON-GRAVITY PRESENTATION OF A LIQUID DROPLET

(76) Inventor: Gary L. Hanley, 39 Rockland St., Malone, NY (US) 12953

( * ) Notice: Subject to any disclaimer, the term of this patent is extended or adjusted under 35 U.S.C. 154(b) by 317 days.

(21) Appl. No.: 10/314,643

(22) Filed: Dec. 9, 2002

(65) Prior Publication Data
US 2004/0111070 A1 Jun. 10, 2004

(51) Int. Cl.$^7$ .............................................. A61M 35/00
(52) U.S. Cl. ........................ 604/295; 604/294; 604/298; 604/300; 604/301; 604/302
(58) Field of Search ................................. 604/294, 295, 604/298, 301, 300, 302

(56) References Cited

U.S. PATENT DOCUMENTS

| | | |
|---|---|---|
| 889,810 A | 6/1908 | Robinson |
| 2,277,936 A | 3/1942 | Rosenblatt .................. 221/148 |
| 2,919,696 A | 1/1960 | Rinaldy ....................... 128/303 |
| 3,756,478 A | 9/1973 | Podell et al. ................ 222/420 |
| 3,910,618 A | 10/1975 | Massenz .................. 294/1 CA |
| 4,550,866 A | 11/1985 | Moore ......................... 222/420 |
| 4,629,456 A | 12/1986 | Edwards ..................... 604/300 |
| 4,927,062 A | 5/1990 | Walsh ......................... 222/420 |
| 4,968,310 A | 11/1990 | Menchel et al. ............ 604/295 |
| 5,040,706 A | 8/1991 | Davis et al. ................. 222/541 |
| 6,041,978 A | 3/2000 | Hagele ........................ 222/420 |
| 6,129,248 A | 10/2000 | Hagele ........................ 222/420 |
| 6,197,008 B1 | 3/2001 | Hagele ........................ 604/295 |
| 6,386,394 B1 | 5/2002 | Vollrath et al. ............. 222/207 |

*Primary Examiner*—Jacqueline F. Stephens
(74) *Attorney, Agent, or Firm*—Downs Rachlin Martin PLLC

(57) ABSTRACT

A device (10) for non-gravity presentation of a droplet (16) of a liquid (12). The device includes an applicator (20) for forming the droplet and a squeeze-type bottle (18) that contains the liquid used to form the droplet. The applicator includes an upwardly-facing presentation surface (36) upon which the droplet is formed. One or more capillary tubes (38) communicate liquid from inside the bottle to the presentation surface via an uptake tube (40) when a user squeezes the bottle. Each capillary tube has a diameter of no greater than about 0.0787 inch (2 mm). Once the droplet has been formed, the user may tilt the device up to a critical tilt angle $\alpha_{critical}$, above which the droplet will fall from the presentation surface. When the device is tilted to a tilt angle $\alpha$ less than or equal to the critical tilt angle, capillary attraction between the droplet and the capillary tube(s) retains the droplet on the presentation surface. The device may be used to deliver a liquid agent to an eye (14) and eliminates the need for the person receiving the agent to tilt his/her head backward. Rather, the person may tilt his/her head forward, and optionally tilt the device to a tilt angle less than or equal to the critical tilt angle, to contact the droplet with the eye.

46 Claims, 12 Drawing Sheets

DEVICE FOR NON-GRAVITY PRESENTATION OF A LIQUID DROPLET

FIELD OF THE INVENTION

The present invention generally relates to the field of dispensers for dispensing a liquid in droplet form. More particularly, the present invention is directed to a device for non-gravity presentation of a liquid droplet for human and veterinary ophthalmic delivery and other applications.

BACKGROUND OF THE INVENTION

Various liquid agents are routinely administered to one or both eyes of a human via eyedrops for a variety of reasons. Examples of these agents include medicaments, moisturizers, irrigators, dilators, and anesthetics, among others. Some of these agents are typically self-administered, i.e., administered by the person receiving the agent, and others of these agents are typically administered by a health care professional. Regardless of who administers the agents, the administration is commonly accomplished using a squeeze bottle type applicator having a generally frusto-conical applicator tip.

To administer an agent to an eye using such an eyedrop applicator, the person receiving the eyedrop typically must tilt his/her head backward or be in a supine or otherwise reclined position. These are often awkward positions for the person, particularly if the person is self-administering the eyedrop. In addition, when the person is self-administering the eyedrop, he/she often has difficulty positioning the applicator over the eye so that the eyedrop is administered to the proper location. While in one of these awkward positions, it is also difficult for the person to determine how large the droplet, or portion thereof, is that actually reaches the eye. Thus, the person does not know whether or not he/she has administered the agent in the proper amount. Complicating this uncertainty in knowing how much of the agent reached the eye due to not being able to position the applicator properly is the fact that most commercially available eyedrop applicators do not have any precise means for metering the size of each eyedrop, thereby controlling the amount of agent dispensed.

Another drawback of most conventional squeeze-type eyedrop applicators is that some users have difficulty controlling the amount of pressure they use when squeezing the container and often dispense far more of the agent than is necessary. This can result in much waste of the agent, which, depending on the particular agent, can be expensive. Some elderly people and others having diminished fine motor control are the groups of people that appear to have the most difficulty in controlling the amount of agent dispensed. Often, these groups are among those least likely to be able to afford such waste and among those most likely to self-administer eyedrop agents.

SUMMARY OF THE INVENTION

In one aspect, the present invention is directed to a device for dispensing a droplet of a liquid. The device comprises a container for containing the liquid and an applicator secured to the container and having a presentation surface for presenting the droplet of the liquid. The presentation surface has a tilt angle α relative to a horizontal plane and a critical tilt angle $α_{critical}$ such that when the tilt angle α is 0°, the presentation surface faces upward. A user-actuated mechanism is provided for conveying the liquid to the presentation surface and forming the droplet on the presentation surface when the tilt angle α is any angle from 0° to the critical tilt angle $α_{critical}$.

In another aspect, the present invention is directed to an applicator securable to a container for forming a droplet of a liquid and presenting the droplet to a user. The container has an interior containing the liquid. The applicator comprises a body having an upper end and is adapted to be secured to the container. A presentation surface is formed on the upper end on which the droplet is formed when the applicator is in use. At least one capillary tube having a diameter of less than about 2 mm extends through the body for communicating the liquid between the interior of the container and the presentation surface when the applicator is in use.

In a further aspect, the present invention is directed to a system for applying a droplet to an eye. The system comprises a liquid agent for being applied to an eye and a device for forming a droplet of the liquid agent and presenting the droplet to the eye. The device comprises a container for containing the liquid agent and an applicator secured to the container and having a presentation surface for presenting the droplet of the liquid agent. The presentation surface has a tilt angle α relative to a horizontal plane and a critical tilt angle $α_{critical}$ such that when the tilt angle α is 0°, the presentation surface faces upward. A user-actuated mechanism conveys the liquid agent to the presentation surface and forms the droplet on the presentation surface when the user-actuated mechanism is actuated and the tilt angle α is any angle from 0° to the critical tilt angle $α_{critical}$.

BRIEF DESCRIPTION OF THE DRAWINGS

For the purpose of illustrating the invention, the drawings show a form of the invention that is presently preferred. However, it should be understood that the present invention is not limited to the precise arrangements and instrumentalities shown in the drawings, wherein.

DETAILED DESCRIPTION OF THE DRAWINGS

Figure 1A:
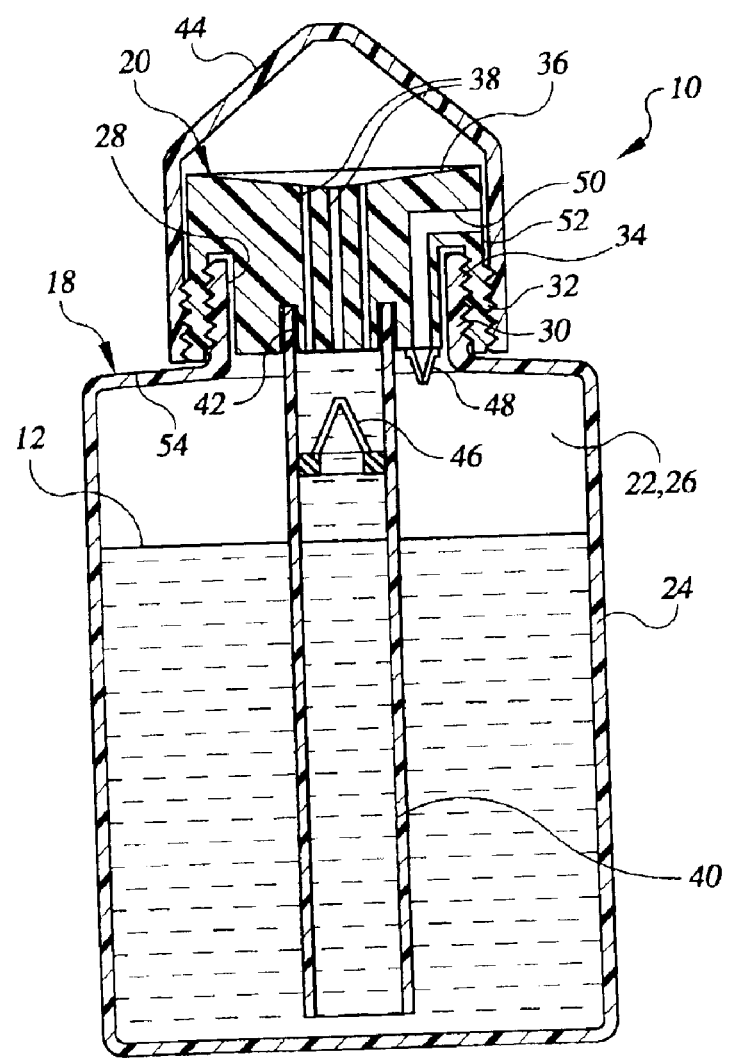
FIGS. 1A–C are cross-sectional views of a device of the present invention showing, respectively, no droplet formed on the presentation surface of the applicator, a droplet being formed on the presentation surface, and a droplet fully formed on the presentation surface and the device tilted at an angle less than the critical tilt angle.
Figure 1B:
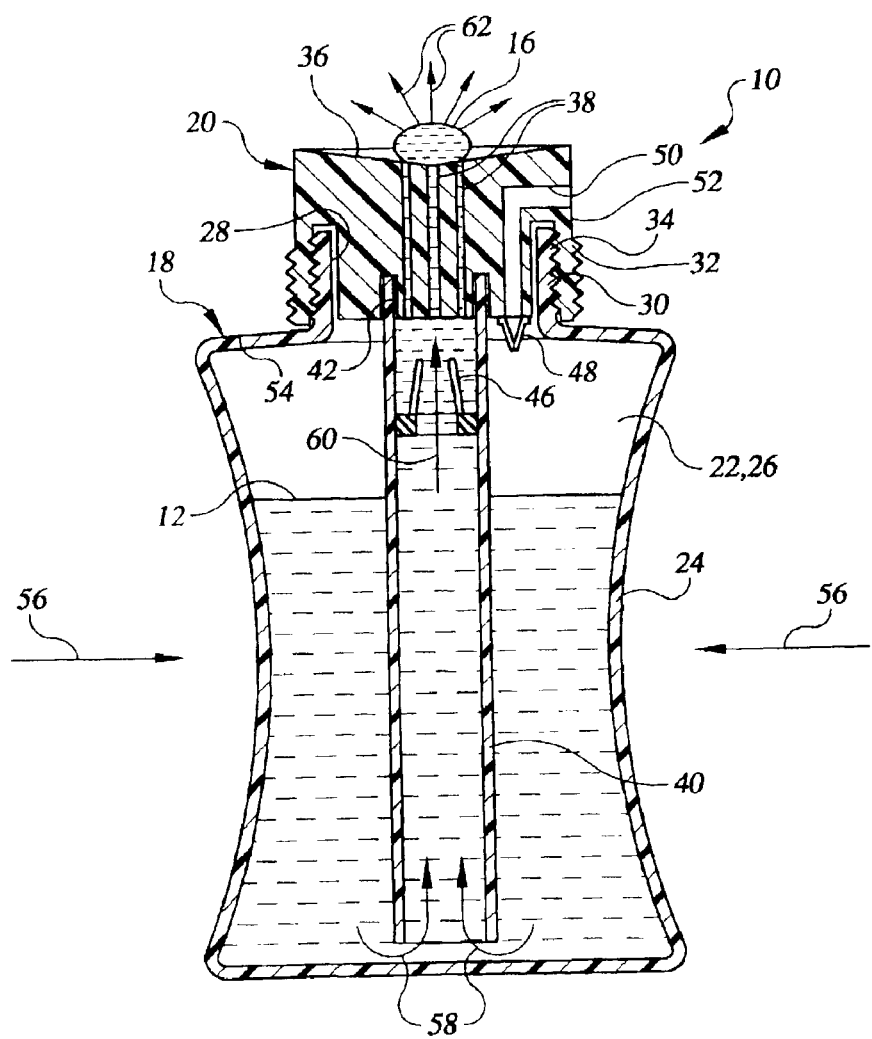
Figure 1C:
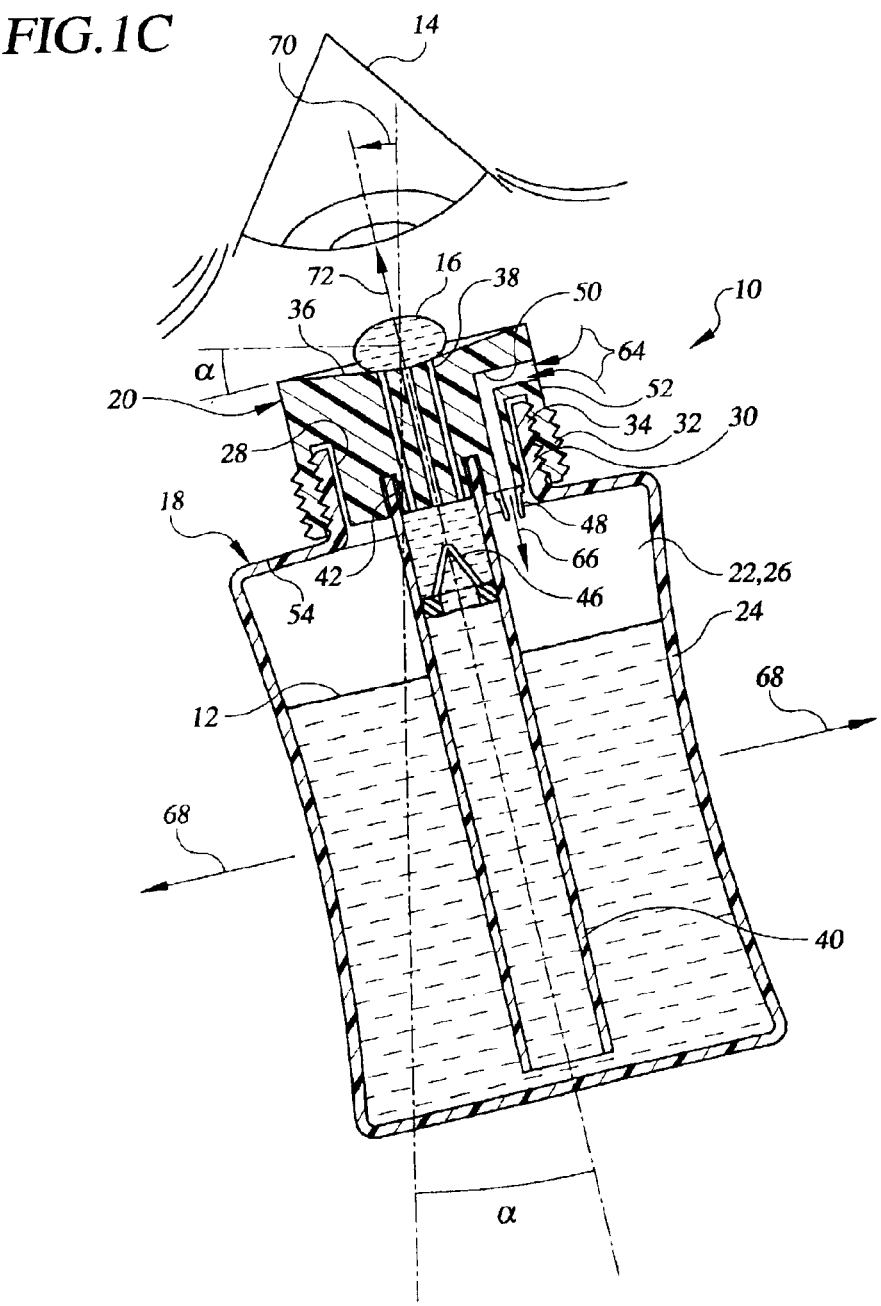

Referring now to the drawings, FIGS. 1A–C show in accordance with the present invention a device, which is generally shown at 10. In the present context, device 10 is particularly adapted for dispensing a liquid 12 to an eye 14 (FIG. 1C), such as the eye of a human or an animal. As used herein and in the claims appended hereto, the term "liquid" shall include any material that is not a solid, gas, or plasma, or is a liquid suspension or any substantially incompressible and flowable combination of materials. Examples of liquid 12 include agents commonly applied to an eye, e.g., eye 14, such as a medicament, moisturizer, irrigator, dilator, and anesthetic, among others. However, those skilled in the art will readily appreciate device 10 of the present invention may be used or modified to dispense other liquids, which may be non-ophthalmic liquids, depending upon the intended use of the liquid.

As described below in detail, device 10 allows a user (not shown) to form a droplet 16 (FIGS. 1B–C) of liquid 12 while the device remains in a generally upright position, which is shown throughout the various figures. Allowing a user to form droplet 16 in this manner permits the user to more precisely control the dispensing of liquid 12 and, thus, the size of the droplet formed. This is useful for any user, but especially useful for a self-administering user who would otherwise typically have to form a droplet on the tip of a conventional eyedrop applicator (not shown) while in an awkward position, such as with his/her head or entire body tilted backward. In other embodiments described below, a device of the present invention may include various other features, such as a metering feature that allows a user to form a droplet having a predetermined size to administer a predetermined dose, and/or a waste-prevention feature that prevents a user from accidentally dispensing more than the desired/needed amount of liquid 12. These and other features are described below.

Device 10 includes a bottle 18 and an applicator 20. Bottle 18 generally defines a cavity 22 for containing liquid 12. In FIGS. 1A–C, bottle 18 is of the squeeze type, i.e., the bottle has a resiliently deformable sidewall 24 that allows a user to deform the sidewall inwardly, thereby causing a pumping action within device 10. In other embodiments, however, bottle 18 may be rigid and the pumping action be provided by other means, such as the button pump, gear pump, and piston pump embodiments shown in FIGS. 6, 7, and 8, respectively. Those skilled in the art will appreciate that cavity 22 may itself be a reservoir 26 for storing liquid 12 or may contain another structure, e.g., a collapsible reservoir (not shown in this embodiment, but see FIGS. 5A–B, element 222), that holds the liquid. The upper end of bottle 18 may include an opening 28 for engaging applicator 20. Opening 28 will typically, but not necessarily, be defined by a neck 30 on bottle 18.

Neck 30 may be of any conventional sort and may include any structure that allows applicator 20 to be secured to bottle 18. In the embodiment shown, applicator 20 engages bottle 18 and is secured thereto via mating threads 32, 34 on the applicator and neck 30, respectively. However, those skilled in the art will appreciate applicator 20 may be secured to bottle 18 or neck 30 in another way, such as by snap fit or interference fit, among others. A seal (not shown), such as a gasket, may be provided between bottle 18 and applicator 20 to inhibit liquid 12 and gas inside cavity 22 from escaping, and air outside the cavity from entering, the cavity between neck 30 and applicator 20. Those skilled in the art will understand the variety of ways applicator 20 may be secured to bottle 18, such that an exhaustive recitation of alternatives is not necessary for those skilled in the art to appreciate the broad scope of the present invention.

Applicator 20 may include a presentation surface 36 upon which droplet 16 forms and one or more capillary tubes 38 extending from the presentation surface generally to cavity 22 of bottle 18. In the embodiment shown in FIGS. 1A–C, presentation surface 30 is circular in shape and has a concave contour. However, presentation surface 36 may be any shape, such as oval or rectangular, among others, and have any other contour desired, such as convex, flat, and various combinations of convex, concave, and/or flat, among others. Presentation surface 36 may, but need not, be hydrophobic to liquid 12 so as to cause droplet 16 to be more spherically shaped than if the presentation surface were hydrophilic to the liquid. Applicator 20 may be made of any suitable material, such as plastic or hard rubber, among others. If it is desired that presentation surface 36 be hydrophobic, it may be coated or otherwise treated to make it so if the material of applicator 20 is otherwise hydrophilic. Moreover, applicator 20 may be formed as a unitary body or from separate parts joined to one another in an appropriate manner. Those skilled in the art will readily understand the many ways in which applicator 20 may be formed, such that a detailed description is not necessary.

The ability of device 10 to retain droplet 16 on presentation surface 36 when the device is tilted at a tilt angle $\alpha$, e.g., as shown in FIG. 1C, is generally a function of the size of droplet 16, number of capillary tubes 38 provided, diameter of each capillary tube, and the length of each capillary tube. This retention is also a function of the properties of liquid 12, e.g., viscosity, surface tension, specific gravity, and mass density. Generally, the capillary attraction forces within each capillary tube 38 interact with the similar attractive forces within droplet 16 so as to cause the droplet to be retained on presentation surface 36 up to a certain tilt angle $\alpha$ of device 10, which may be referred to as the critical tilt angle, $\alpha_{critical}$. Depending upon the type of liquid 12, the size of droplet 16, and the configuration of the one or more capillary tubes 38, critical tilt angle $\alpha_{critical}$ may be any value from 0 to 180°. Thus, depending upon design parameters, device 10 may be used to dispense droplet 16 to eye while the device is perfectly upright, as shown in FIGS. 1A and 1B, while the device is completely inverted from the orientation shown in FIGS. 1A and 1B, or any orientation in between.

In general, the larger the diameter of each capillary tube 38 for droplet 16 of a certain size and liquid 12, the smaller $\alpha_{critical}$ will be. Conversely, of course, the smaller the diameter of each capillary tube 38, the larger critical tilt angle $\alpha_{critical}$ will be. Also, for a given diameter of each capillary tube 38, the greater the number of capillary tubes 38 provided, the larger $\alpha_{critical}$ will be. In terms of the size of droplet 16, at a particular $\alpha_{critical}$, generally the more capillary tubes 38 provided, the larger the droplet can be. Similarly, the length of each capillary tube 38 must be long enough to develop the forces necessary to prevent droplet 16 from disengaging applicator 20. In general, the required length will vary depending upon the capillary constant for the particular liquid 12, the number of capillary tubes 38 provided, the desired size of droplet 16, and the desired critical angle.

Accordingly, when designing device 10 for a specific application that utilizes a particular liquid 12, the designer must select the appropriate number and diameters of capillary tubes 38 to achieve the desired size of droplet 16 and $\alpha_{critical}$. For example, when device 10 is used as an applicator for applying a droplet of a saline solution to an eye, it may be desirable to have droplet 16 contain 20 µl of liquid 12 and the device achieve a $\alpha_{critical}$ of at least 90° so that a user may apply the droplet to the eye at any angle from 0°, i.e., the device perfectly upright, up to and including 90°, i.e., the device perfectly horizontal. To achieve this particular size of droplet 16 and $\alpha_{critical}$, the designer may provide, e.g., several capillary tubes 38 each having a diameter of about 0.0472 inch (1.2 mm). Those skilled in the art will appreciate that this is but one solution to providing an applicator capable of providing a droplet 16 containing 20 µl up to a tilt angle α of 90°. For example, those skilled in the art will understand that providing more capillary tubes 38 and/or capillary tubes having smaller diameters could achieve the same results. Generally, however, each capillary tube 38 will have a diameter no larger than about 0.0787 inch (2 mm) regardless of the number of capillary tubes provided and may have a diameter at least as small as about 0.0118 inch (0.3 mm). For most ophthalmic applications, droplet will contain no more than about 60 µl of liquid 12.

Device 10 may also include an uptake tube 40, or other structure, for communicating liquid 12 from reservoir 26 to capillary tubes 38 when bottle 18 is squeezed. Uptake tube 40 may be made of any suitable material, such as plastic, among others. As those skilled in the art will appreciate, uptake tube 40 may be engaged with applicator 20 in any suitable manner, such as the press-fit engagement with a circular groove 42 formed in the applicator.

Optionally, device 10 may include a cap 44 for protecting presentation surface 36 and/or preventing the device from dispensing liquid 12 when the device is not in use. Cap 44 may be threadedly engaged with applicator 20 as shown, or may be otherwise suitably engaged with the applicator or bottle 18.

Device 10 may also optionally include a first valve 46 for inhibiting droplet 16 formed on presentation surface 36 from being sucked back into the device when a user releases his/her squeeze on bottle 18 and a second valve 48 for allowing air to enter the bottle upon release of the squeeze so that the bottle may regain its undeformed shape. Each of first and second valves 46, 48 may be any suitable one-way valves, such as a duckbill valve, cross-slit valve, flapper valve, or ball valve, among others. First valve 46 may be located in any suitable location, such as within uptake tube 40. Depending upon the design of the various components, first valve may be located elsewhere.

Second valve 48 may also be located in any suitable location, such as attached to applicator 20 as shown. In this case, applicator 20 may include an air-intake passageway 50 extending between cavity 22 and a surface of the applicator exposed to the ambient environment when device 10 is in use, such as the side surface 52 of the applicator as shown. An advantage of providing air-intake passageway 50 in the location shown, or similar location, is that it is protected by cap 44 when the cap is engaged with device 10 during periods of non-use. Of course, second valve 48 may be located elsewhere, e.g., on sidewall 24 or upper end wall 54 of bottle 18, such that it fluidly communicates with cavity 22 via a corresponding opening (not shown) in the bottle. Those skilled in the art will appreciate the various locations first and second valves 46, 48 may be placed to achieve the desired functions.

Device 10 may be used as follows. Referring to FIG. 1A, a user would typically first remove cap 44 to expose presentation surface 36. Referring to FIG. 1B, while holding device 10 generally upright, i.e., with the device not tilted at all or tilted to a tilt angle α less than $\alpha_{critical}$, the user gently squeezes bottle 18 (arrows 56) to force liquid 12 up uptake tube 40 (arrows 58), through first valve 46 (arrow 60), and through capillary tubes 38 so that droplet 16 forms on the presentation surface. As the user continues to squeeze bottle 18, droplet 16 continues to grow in size, as indicated by arrows 62. Referring to FIG. 1C, when the user determines droplet 16 is the desired size, the user may release his/her squeeze on bottle 18, thereby closing first valve 46 and opening second valve 48 to allow air to flow into air-intake passageway 50 (arrows 64), through the second valve 48 (arrows 66), and into cavity 22. The flow of air into cavity 22 allows bottle 18 to return to its undeformed shape, as indicated by arrows 68.

Then, in the case of device 10 being used as an applicator for applying an agent to an eye, such as eye 14, if the device is not already tilted to a desired tilt angle α, the user may tilt the device to a suitable tilt angle α (arrow 70), tilt his/her head forward, and move the device toward the eye (arrow 72) so that droplet 16 contacts the eye. Alternatively, the user may hold device 10 steady in a tilted or untilted position and move eye 14 into contact with droplet 16. It is noted that the user need not tilt device at all, if desired. When droplet 16 contacts eye 14 and the natural liquid film formed thereon, the surface tension of liquid 12 within the droplet attracts the droplet to the eye, thereby transferring the droplet to the eye. In an alternative embodiment not having first valve 46, or other means for inhibiting droplet 16 from being sucked back into device 10, the user may simply hold bottle 18 in its squeezed configuration while he/she applies the droplet to eye 14.

FIGS. 2A–B, 3 and 4 show an alternative embodiment of a device 110 according to the present invention. Similar to device 10 of FIGS. 1A–C, device 110 may generally include a squeeze-type bottle 112, an applicator 114 secured to the bottle, and an uptake tube 116 engaging the applicator and extending into a cavity 118, which is generally defined by the bottle. Again, each of these components may be made of any suitable material, such as plastic. Applicator 114 may include a presentation surface 120 and one or more capillary tubes 122 extending from the presentation surface to the interior of uptake tube 116. Capillary tube 122 may be sized and provided in a certain number as described in connection with capillary tubes 38 of FIGS. 1A–C. Device 110 is shown as having only a single capillary tube 122.

However, unlike device 10 of FIGS. 1A–C, device 110 includes an internal stop 124 located within cavity 118 for preventing a user from squeezing bottle 112 more than a predetermined amount. Depending upon the design of device 110, internal stop 124 may be used to meter the size of droplet 126 formed on presentation surface 120, allow the user to easily maintain the bottle 112 in its squeezed state to inhibit the droplet from being sucked back into the device, and/or protect a user from unintentionally dispensing a large amount of liquid 128. To provide these functions, internal stop 124 may include one or more contacts 130A, 130B that contact corresponding internal surfaces of sidewall 132 of bottle 112 when a user squeezes the bottle a predetermined amount.

Figure 2A:
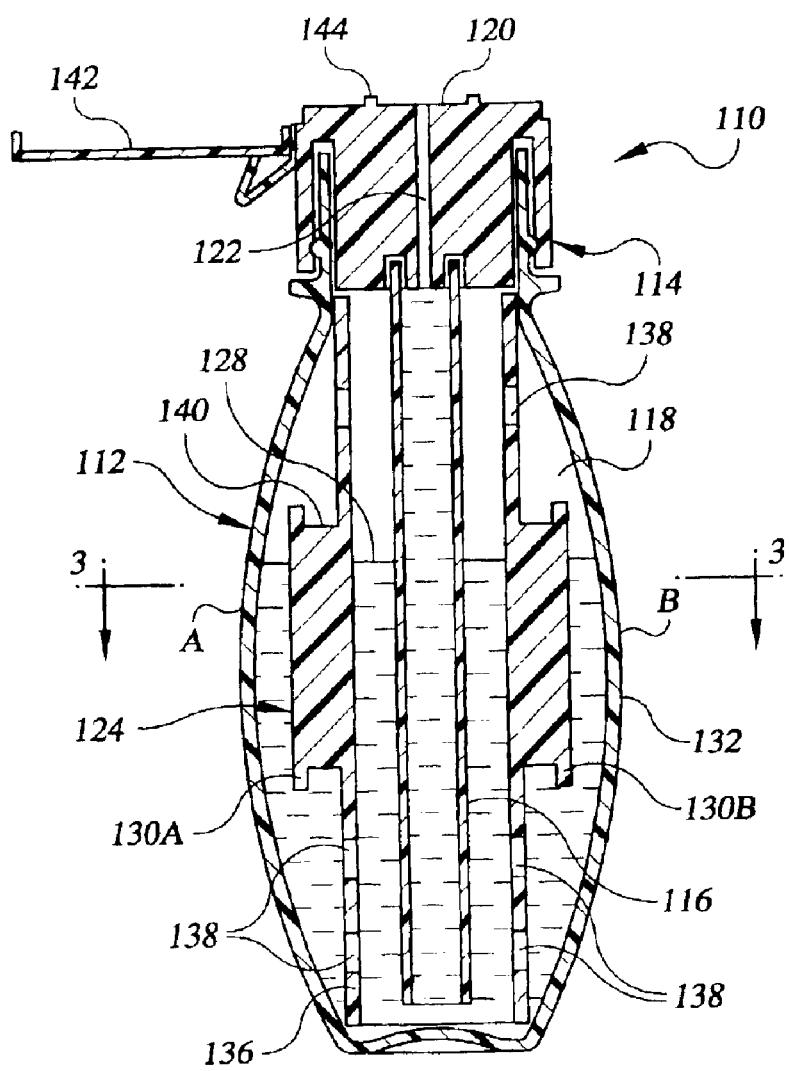
FIGS. 2A–B are cross-sectional views of a device of the present invention having an internal stop and showing, respectively, the squeeze bottle in a relaxed state and a fully-squeezed state.
Figure 2B:
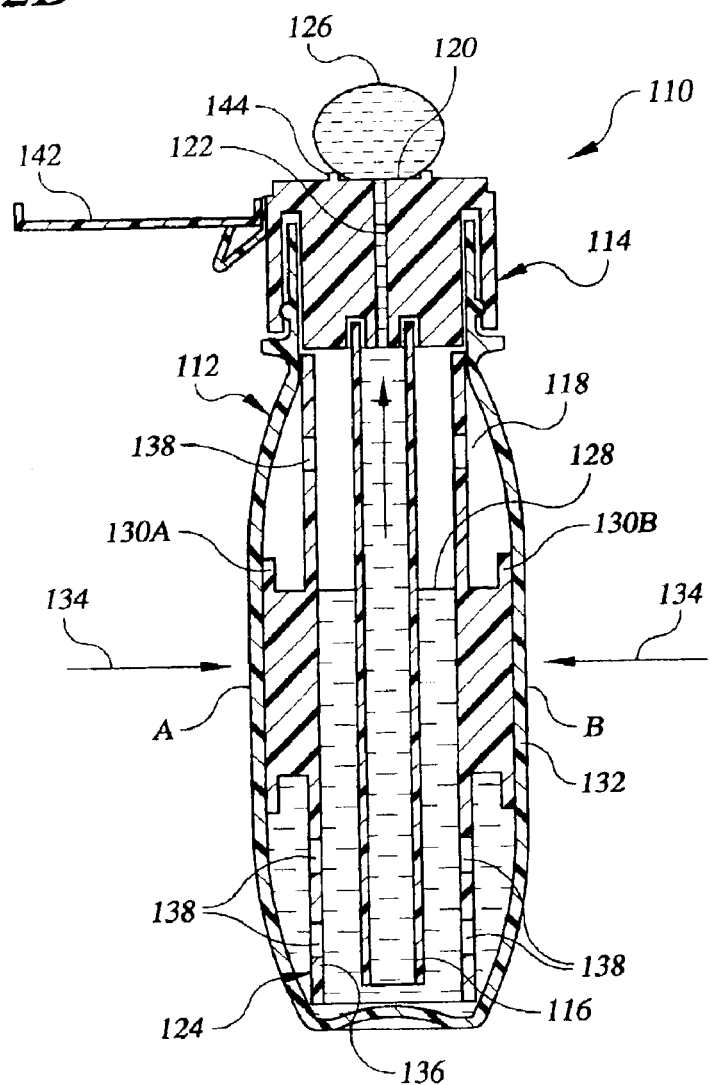

In the particular embodiment shown, bottle 112 is configured to be squeezed only in the direction of arrows 134 of FIG. 2B. Accordingly, internal stop 124 includes two contacts 130A, 130B for contacting opposing internal surfaces of sidewall 132 when bottle 112 is squeezed. However, those skilled in the art will appreciate that other embodiments of bottle 112 may require internal stop 124 to have other configurations. For example, a cylindrical bottle (not shown)

configured to be squeezed generally from any two generally opposing locations around the circumference of the cylindrical shape may have a cylindrical internal stop that is coaxial with the bottle so that the internal stop functions regardless of the angular position around the circumference of the bottle at which a user applies a squeeze. In addition, another embodiment of bottle 112 may be configured so that only one portion of sidewall 132 may be squeezed to form droplet 126. For example, one side of bottle 112, e.g., side A of the two opposing sides A and B, may be made so that it does not deform substantially when the bottle is squeezed. This may be accomplished, e.g., by making sidewall 132 thicker on side A, reinforcing the sidewall on side A, or making the sidewall on side A from a different, more rigid material than side B. In this case, the other side, side B, would be the only side deformable by squeezing bottle 112. Accordingly, internal stop 124 would need only one contact, i.e., contact 130B.

Figure 3:
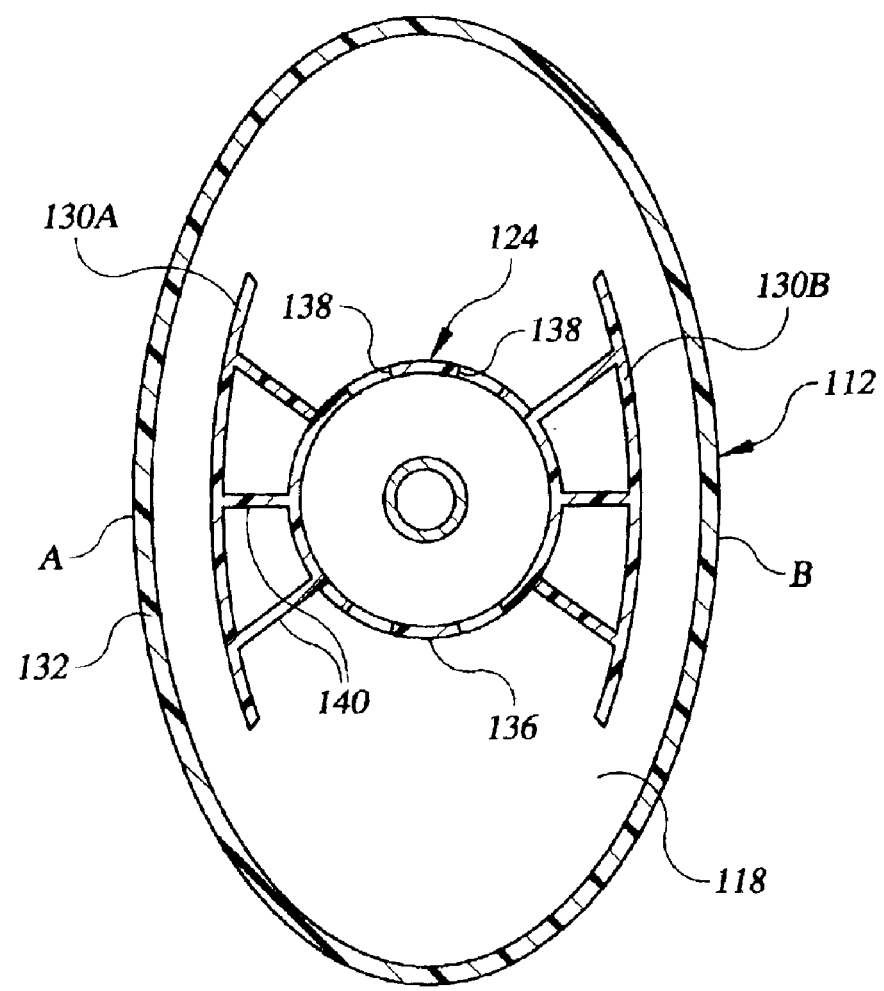
FIG. 3 is a cross-sectional view of the device of FIGS. 2A–B as taken along line 3–3 of FIG. 2A.

Internal stop 124 may be formed integrally with either bottle 112, applicator 114, or both, or may be formed separately from both. If formed separately, internal stop 124 may be fixedly attached to one or both of these components to prevent it from moving relative thereto. However, internal stop 124 need not be attached to either bottle 112 or applicator 114. This is shown in FIGS. 2A–B and 3. In this case, internal stop 124 may include an appropriate structure for stabilizing the internal stop within cavity 118 so that it does not move, or moves only slightly, relative to bottle 112. For example, internal stop 124 may include a central support 136 to inhibit contacts 130A, 130B from moving side-to-side and up-and-down relative to bottle 112. Central support 136 may be perforated or otherwise contain openings 138 that allow liquid 128 to flow through the central support. Secondary supports 140 may be provided to support contacts 130A, 130B off of central support 136. While only one embodiment of internal stop 124 has been presented, those skilled in the art will easily recognize the variety of configurations that the internal stop may have, such that numerous examples need not be provided herein.

As mentioned, internal stop 124 may provide a metering function that allows a user to form droplet 126 having a desired, predetermined size. This may be accomplished by locating the contacts 130A, 130B at a certain distance from the portions of sidewall 132 deformed when bottle 112 is squeezed to form droplet 126. This distance generally corresponds to the volume of liquid 128 needed to make droplet 126 the desired size. Once uptake tube 116 and capillary tube 122 have been primed, i.e., filled with liquid 128, each squeeze of bottle 112 sufficient to cause sidewall 132 to engage contacts 130A, 130B will form droplet 126 of the desired size upon presentation surface 120.

If desired, device 110 may optionally be provided with various valves, such as first and second valves 46, 48 of FIGS. 1A–C, that would inhibit droplet 126 from being sucked back into the device and bottle 112 to return to its undeformed shape upon release of the squeeze. Otherwise, internal stop 124 may allow the user to easily maintain bottle 112 in its squeezed state by keeping sidewall 132 of the bottle engaged with contacts 130A, 130B while droplet 126 is being applied to an eye or other structure, thereby not causing suction with capillary tube 122 that would suck the droplet back into device 110.

If internal stop 124 is designed to only prevent a user from dispensing an excessive amount of liquid 128, contacts 130A, 130B may be located farther from sidewall 132 than the distance that corresponds to the displacement of the sidewall needed to form droplet 126 of a predetermined size. In other words, in a non-metering scenario, contacts 130A, 130B can be located at a location different from the location where they would be provided in a metering scenario so that sidewall 132 may be displaced farther than the amount needed to form droplet 126 of proper size. Such positioning of contacts 130A, 130B would allow some waste of liquid 128, but would not allow excessive waste. The designer of a particular embodiment of device 110 would have to determine the dividing line between an acceptable amount of waste and too much waste. Like the metering embodiment discussed above, a non-metering embodiment of device 110 may optionally be provided with other features, such as means for inhibiting droplet 126 from being sucked back into bottle 112 and/or allowing air to enter the bottle upon the user's release of the squeeze. For example, device 110 may include one or both of the first and second valves 46, 48 discussed above in connection with FIGS. 1A–C.

Also, in lieu of threaded cap 44 of FIGS. 1A–C, device 110 may include a flip-type lid 142 for protecting presentation surface when the device is not in use. Of course, another type of protective cover, such as cap 44 of FIGS. 1A–C or other cover, or no cover at all, may be used.

Figure 4:
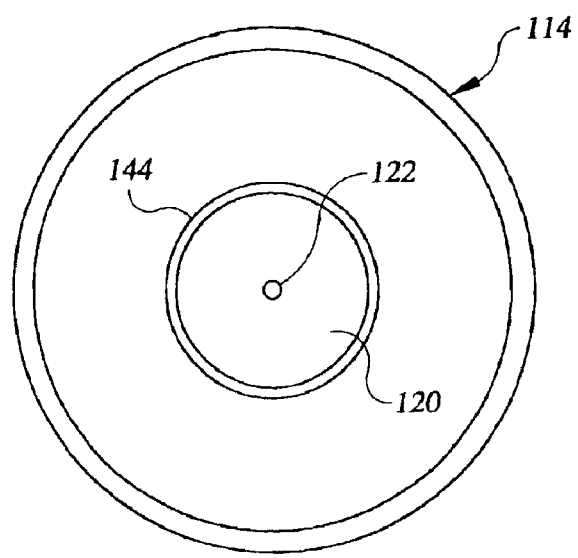
FIG. 4 is a plan view of the applicator tip of the applicator of FIGS. 2A–B showing an indicia on the presentation surface that provides a visual indication of the proper size droplet.

Referring now to FIGS. 2A–B and FIG. 4, applicator 114 may optionally include an indicia 144 on presentation surface 120 that visually indicates to a user the proper size of droplet 126 for a particular application. Indicia 144 may be any suitable visual indicator, such as the raised annulus shown. Indicia may also be recessed and/or painted or otherwise marked on presentation surface. If a particular embodiment of device 110 is intended to provide droplets of two or more predetermined sizes, a separate indicia 144 may be provided for each size.

Figure 5A:
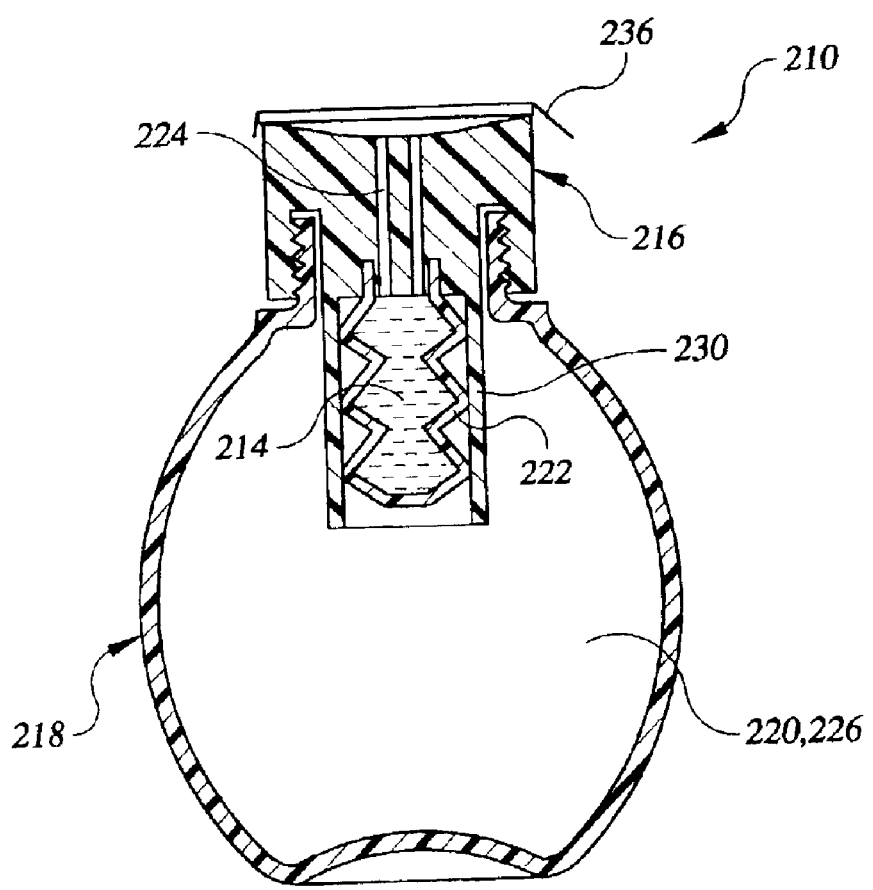
FIGS. 5A–B are cross-sectional views of a single-use device of the present invention showing, respectively, the device prior to, and during, use.
Figure 5B:
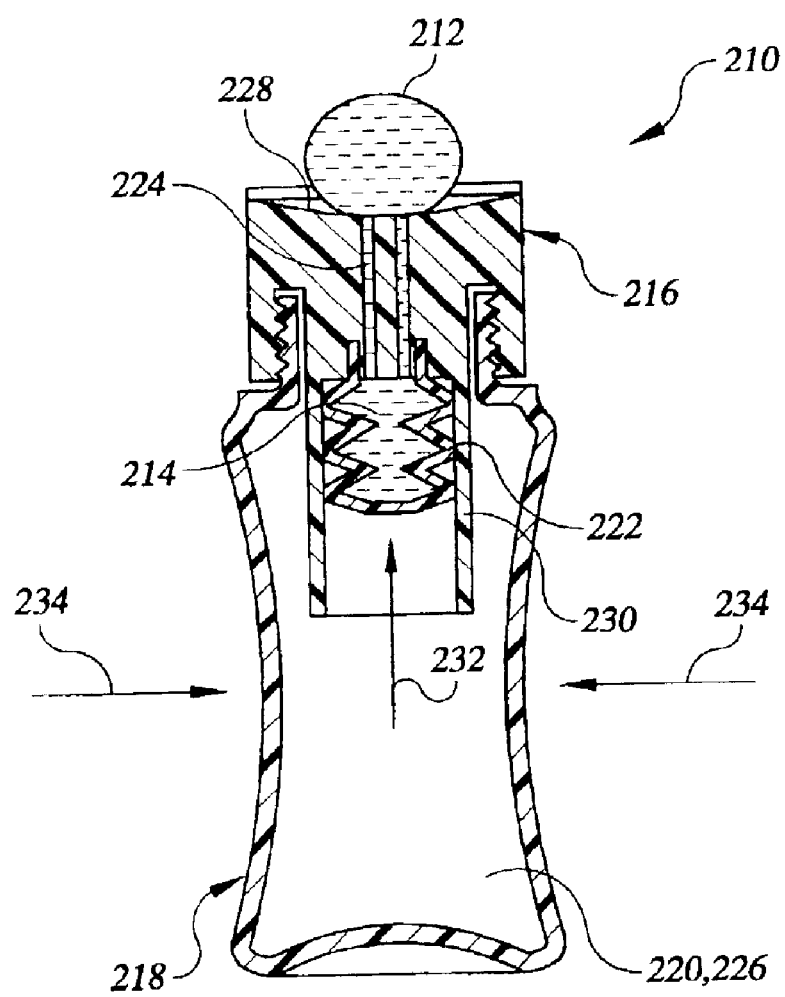

FIGS. 5A–B show another device 210 of the present invention. Whereas devices 10, 110 of FIGS. 1A–C and 2A–B are generally, but not necessarily, designed for multiple use, i.e., dispensing a relatively large number of droplets before the dispensed liquid is depleted, device 210 of FIGS. 5A–B is generally, but not necessarily, designed for single use, i.e., dispensing only a single droplet 212 of liquid 214 during its lifetime, or several droplets successively, e.g., when a single dosage requires application of more than one droplet. Similar to devices 10, 110 of FIGS. 1A–C and 2A–B, device 210 may include an applicator 216 and a squeeze-type bottle 218. However, in this embodiment, cavity 220 of bottle 218 may contain a reservoir 222 holding liquid 214 and in fluid communication with capillary tubes 224.

Reservoir 222 may generally contain an amount of liquid 214 the same as the amount of liquid in the one or several droplets 212 to be dispensed during use, or somewhat greater than this amount to account for any amount of liquid not dispensed, e.g., the liquid that remains in capillary tubes 224 and/or in reservoir due to its collapsed configuration. Reservoir 222 may be any suitable structure for containing liquid, such as a bellows-type container. In the present example, the amount of liquid 214 required to be dispensed is relatively small, e.g., 30 $\mu$l, resulting in a commensurately small reservoir 222. However, so that device 210 has a manageable size, i.e., a size such that a user can manipulate the device conveniently with his/her fingers, bottle 218 may be relatively much larger than reservoir 222. This creates an airspace 226 between bottle 218 and reservoir 222 that may be fluidly sealed with respect to both the ambient environment of device 210 and the interior space of the reservoir. Thus, when a user squeezes bottle 218, the pressure within airspace 226 increases, causing reservoir 222 to collapse, thereby forming droplet 212 on presentation surface 228.

Device 210 may optionally include a guide 230 for controlling collapse of reservoir 222 (arrow 232) when a user squeezes bottle 218 (arrows 234) to dispense liquid 214 and form droplet 212. Device 210 may also optionally include a removable seal 236 for protecting presentation surface 228, capillary tubes 224, and liquid 214 from contamination until a user desires to administer the liquid. Of course, device 210 may include other features, including an internal stop 124 (FIGS. 2A–B), means for inhibiting droplet 212 from being sucked back into the device (FIGS. 1A–C), means for allowing bottle 218 to return to its undeformed shape after release of a squeeze while the droplet is on presentation surface 228 (FIGS. 1A–C) and/or a cap (FIG. 1A) or flip-type lid (FIGS. 2A–B), among others.

Figure 6:
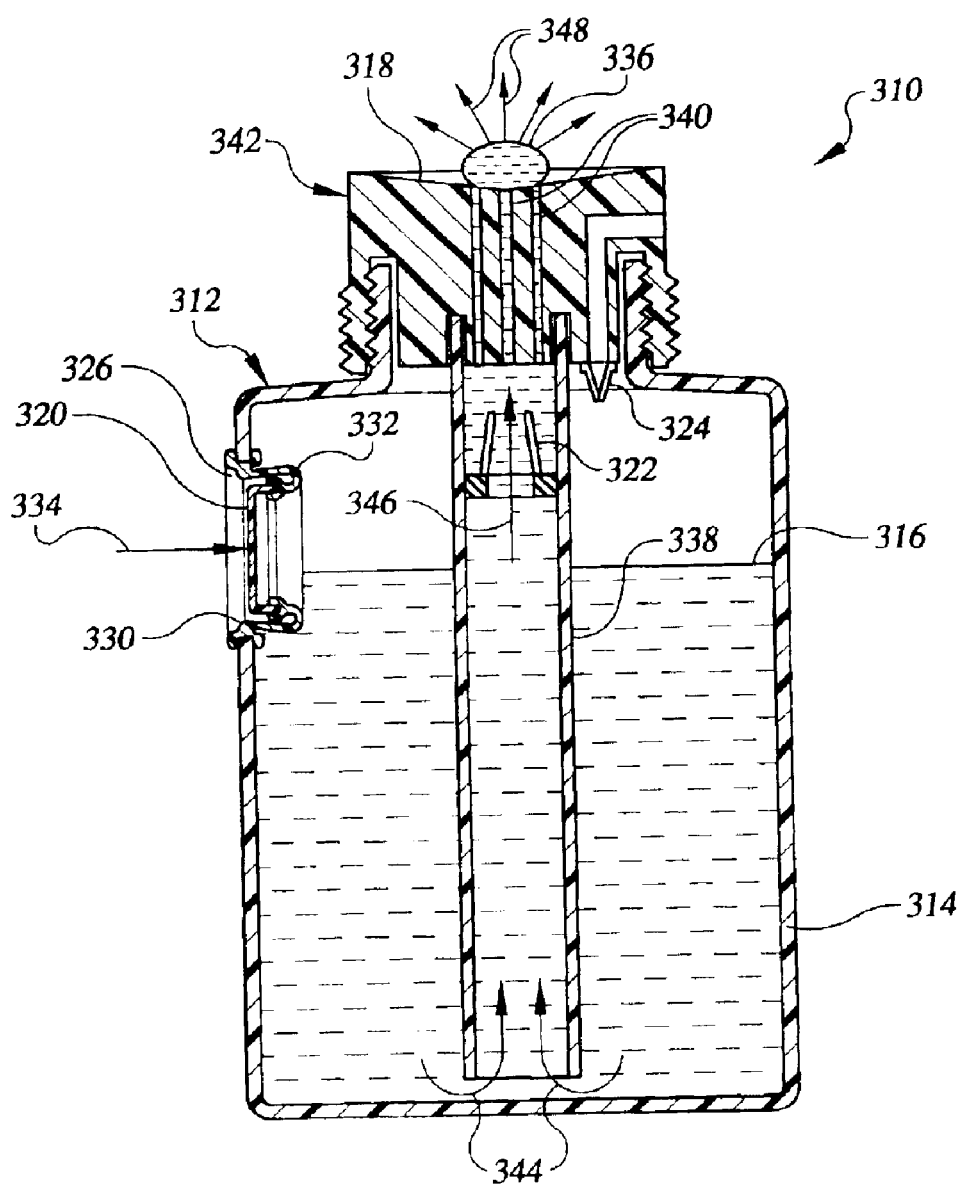
FIG. 6 is a cross-sectional view of a device of the present invention having a rigid bottle and a depressible button for pumping the liquid to the presentation surface of the applicator.

FIG. 6 shows a device 310 that is generally similar to device 10 of FIGS. 1A–C. However, in lieu of the squeeze-type bottle 18 of device 10, bottle 312 of device 310 is relatively rigid. That is, sidewall 314 of bottle 312 will not deform substantially when a user squeezes the bottle. Thus, the bottle 312 does not provide a pumping action for conveying liquid 316 to presentation surface 318. Rather, device 310 includes a depressible button 320 that works in conjunction with first and second one-way valves 322, 324 to pump liquid 316 to presentation surface 318.

Depressible button 320 may take any form, such as the rigid button arrangement shown, wherein the button is located within an opening 326 in sidewall 314 and is fluidly sealed to the sidewall by a flexible membrane 330 having one or more folds 332 that allow the button to be depressed into bottle 312, as shown by arrow 334. Alternatively, depressible button 320 may simply be a flexible member (not shown) spanning opening 326 and fluidly sealed to the rigid sidewall 314 around the periphery of the opening. Such a flexible member would include the situation wherein a particular region of sidewall 314 is made thin enough that a user could readily deform this region inwardly with respect to bottle 312 to create the necessary pumping action.

Depressible button 320 and/or flexible membrane 330 may be designed so that the button may be depressed only a certain amount. This may be done for one or more reasons, including metering the size of droplet 336 and limiting the amount of waste of liquid 316, discussed above in connection with device 110 of FIGS. 2A–B that contains an internal stop (124) that may be configured to provide these same functions. Alternatively, device 310 may include its own internal stop (not shown) positioned inside bottle 312 that would limit the travel of depressible button 320.

Generally, device 310 operates as follows. After uptake tube 338 and capillary tubes 340 have been primed, when a user desires to form droplet 336 on presentation surface 318 of applicator 342, the user pushes depressible button 320 inwardly with respect to bottle 312, as indicated by arrow 334, e.g., using a finger. Generally, this should be done while device 310 is perfectly upright or tilted to tilt angle $\alpha$ less than or equal to $\alpha_{critical}$ (see FIG. 1C) for the particular configuration of capillary tubes 340 and liquid 316 being dispensed. As the user pushes depressible button 320 inwardly, the pressure within device 310 increases, causing liquid 316 within bottle 312 to flow into uptake tube 338 (arrows 344). Liquid 316 within uptake tube 338 then acts against first one-way valve 322 to open this valve, as indicated by arrow 346. The pressure caused by the pushing of depressible button 320 also causes liquid to be forced up capillary tubes 340 and to form droplet 336 (arrows 348). The user continues to push depressible button 320 until droplet 336 is of the desired size.

When droplet 336 is the desired size, the user may then stop pushing depressible button 320. When the user stops pushing depressible button 320, energy stored in flexible member 330 during the pushing process acts to restore the button to its un-depressed position. As depressible button 320 returns to its un-depressed position (not illustrated), first one-way valve 322 closes, preventing droplet 336 from being sucked back into device 310, and second one-way valve 324 opens, substantially equalizing the pressures inside bottle and outside bottle 312. After droplet 336 is formed, the user may then apply the droplet at any tilt angle $\alpha$ from 0° up to $\alpha_{critical}$, as discussed above in connection with FIGS. 1A–C.

Figure 7:
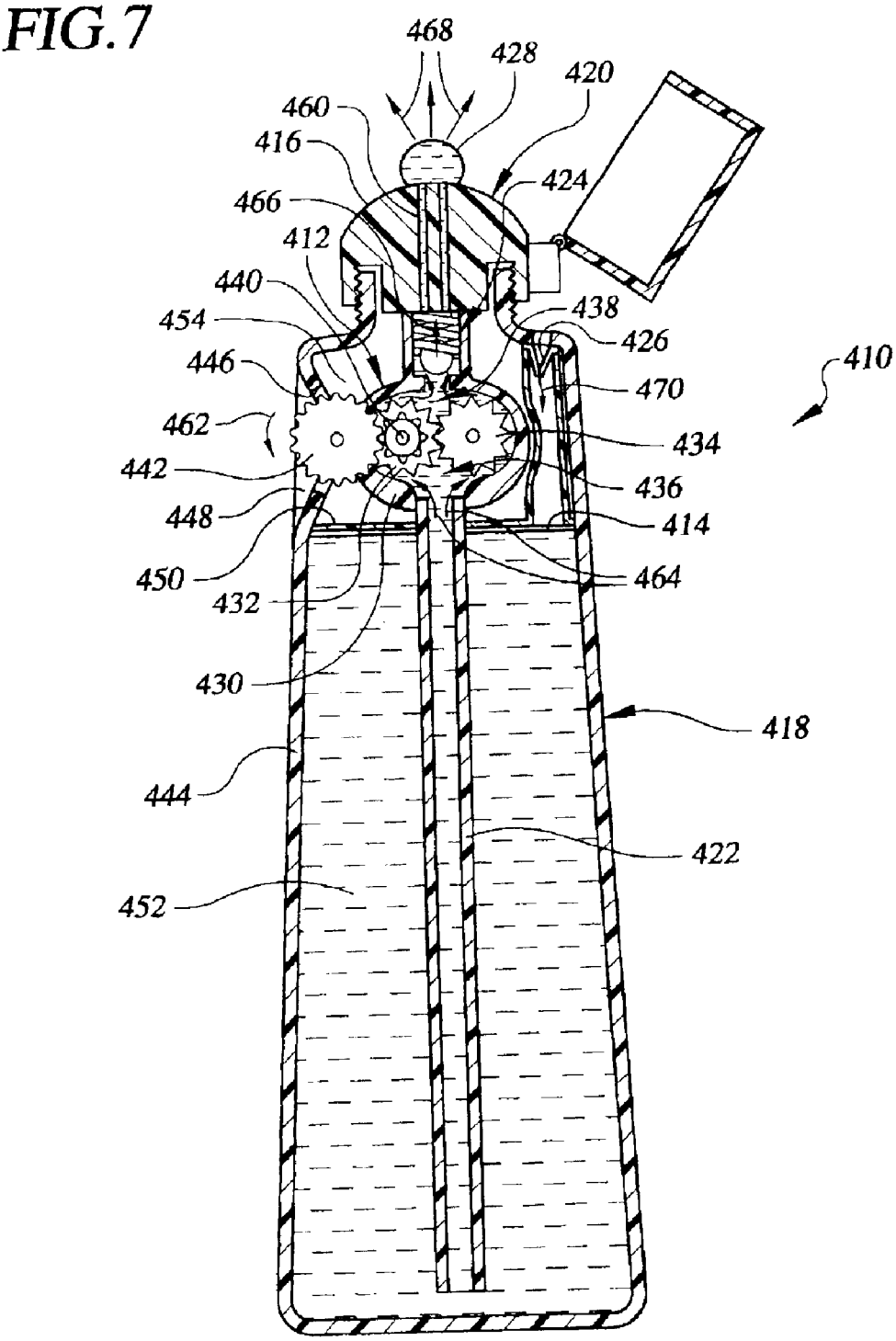
FIG. 7 is a cross-sectional view of a device of the present invention having a rigid bottle and an internal gear pump for pumping the liquid to the presentation surface of the applicator.

FIG. 7 shows a device 410 of the present invention that includes a gear pump 412 for pumping liquid 414 to presentation surface 416. The components of device 410 other than gear pump 412 may generally be the same as in other devices of the present invention described above. That is, device 410 may include a bottle 418, which in this embodiment is typically relatively rigid, an applicator 420, an uptake tube 422, and first and second one-way valves 424, 426. Notable differences between device 410 and the other devices shown thus far include presentation surface 416 having a convex shape, rather than planar or concave, and first one-way valve 424 being a ball-type valve, rather than a duck-bill or other type of one-way valve. It is noted that the convex shape of presentation surface 416 may be desirable for ophthalmic applications, since with this shape it would be least likely for a user to contact presentation surface 416 with his/her eye during administration of droplet 428 to the eye, when compared to the planar and concave shapes shown previously.

Gear pump 412 may be substantially similar to conventional gear pumps. That is, gear pump 412 may generally include a housing 430 and first and second gears 432, 434 that enmesh, and counter-rotate, with respect to one another to pump liquid 414 from the low-pressure side 436 of the pump to the high pressure side 438. A third gear 440 is coupled to the first gear 432 so it rotates in unison with the first gear. As those skilled in the art will understand, FIG. 7 shows gear pump 412 with a portion of housing 430 removed in order to see first and second gears 432, 434. In the actual working device, first and second gears 432, 434 would be enclosed within housing 430, and third gear 440 would be external to the housing and coupled to the first gear through an opening in the housing. The various components of gear pump 412 may be made of any suitable material, such as plastic or metal.

Third gear 440 may enmesh with an actuator wheel 442 rotatably mounted to bottle 418 so that a portion of the wheel extends outside sidewall 444 through an opening 446 so that a user may rotate the wheel, e.g., using his/her thumb, thereby actuating gear pump 412. Actuator wheel 442 may be located within a recess 448 formed in sidewall 444 to inhibit damage to the actuator wheel and/or prevent accidental rotation of the actuator wheel. Since actuator wheel 442 must extend through opening 446 to be accessible to a user and it is typically desired that liquid 414 within bottle 418 be sealed from the environment outside the bottle, the bottle may include a reservoir seal 450 that fluidly seals reservoir 452 from an upper chamber 454 within the bottle that may contain gear pump 412 and a portion of actuator wheel 442.

Actuator wheel 442 may be made of any suitable material, such as plastic or metal. In alternative embodiments, actuator wheel 442 may be replaced with another type of actuator (not shown), such as a linear actuator having a rack for enmeshing with third gear 440, or a lever-arm actuator having an arcuate surface containing teeth for enmeshing with the third gear, among others. Those skilled in the art will appreciate that variety of actuators that may be provided to actuate gear pump 412.

In general, device 410 works as follows to form droplet 428 on presentation surface 416 of applicator 420. Once uptake tube 422 and capillary tubes 460 have been primed with liquid 414, a user rotates actuator wheel 442 in the direction shown by arrow 462, e.g., using his/her thumb or other finger. Typically, but not necessarily, the user will be holding device 410 in a substantially upright orientation while forming droplet 428. However, as discussed above in connection with other devices of the present invention, the user may form droplet 428 when device 410 is at any tilt angle $\alpha$ from $0°$ to $\alpha_{critical}$. The rotating of actuator wheel 442 causes first and second gears 432, 434 to rotate, thereby actuating gear pump 412 to pump liquid 414 from low-pressure side 436 of the pump, as indicated by arrows 464 to the high-pressure side 438. The pressure within liquid 414 on high-pressure side 438 of gear pump 412 causes first one-way valve 424 to open (arrow 466), which allows the liquid to flow through capillary tubes 460 to presentation surface 416 and form droplet 428 thereon, as indicated by arrows 468. As liquid 414 is drawn from reservoir 452 by gear pump 412, second one-way valve 426 opens to allow air outside bottle 418 to be drawn into the reservoir (arrow 470) in order to equalize the pressure inside and outside the bottle.

Actuator wheel 442 and the various components of gear pump 412 may be designed so that one or other particular number of proper actuations of the wheel by a user forms droplet 428 into its desired pre-determined size for the particular application of device 410. Alternatively, presentation surface 416 may include a suitable visual indicia (not shown, but see, e.g., indicia 144 of FIG. 4) for indicating the proper size of droplet 428 so that the user would rotate actuator wheel 442 until the droplet reached the proper size, as determined using the indicia.

Figure 8:
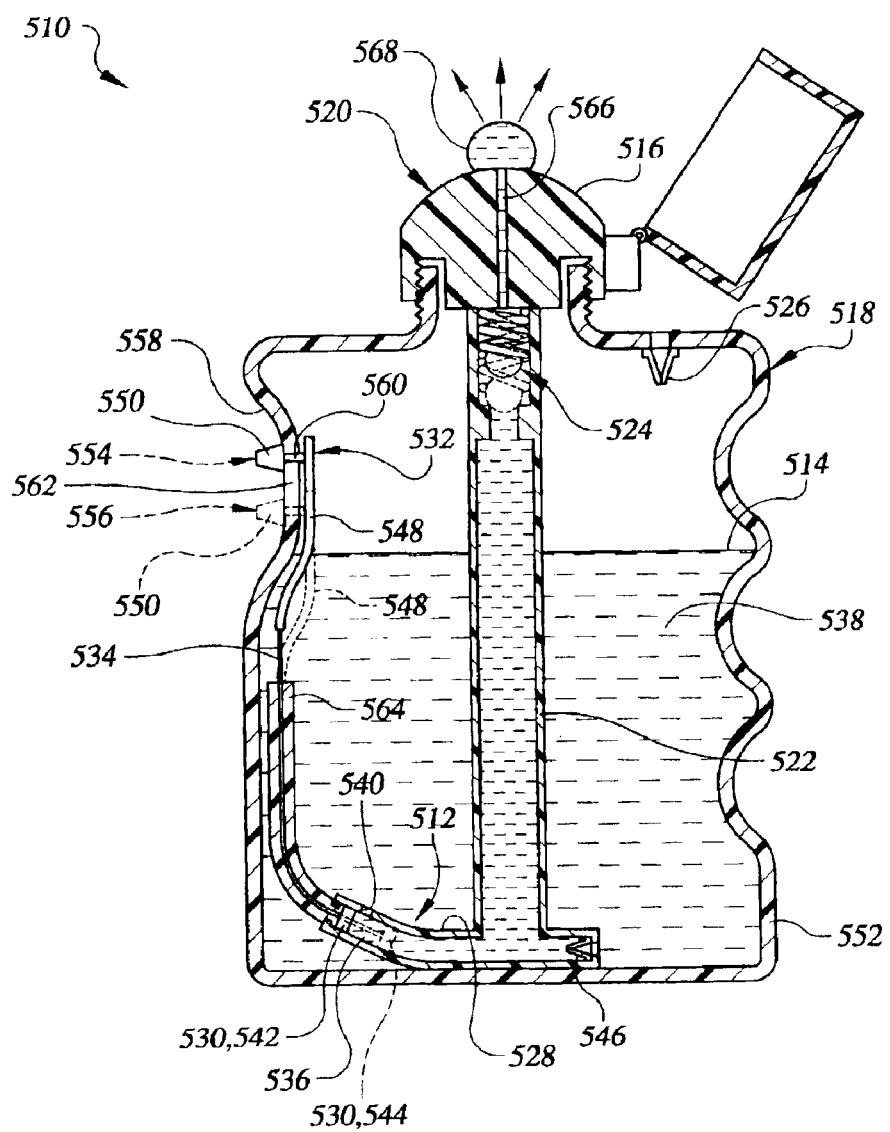
FIG. 8 is a cross-sectional view of a device of the present invention having a rigid bottle and a piston pump for pumping the liquid to the presentation surface.

FIG. 8 shows a device 510 of the present invention that includes a piston pump 512 for pumping liquid 514 to presentation surface 516. The components of device 510 other than piston pump 512 may generally be the same as in other devices of the present invention described above. That is, device 510 may include a bottle 518, which in this embodiment is typically relatively rigid, an applicator 520, an uptake tube 522, and first and second one-way valves 524, 526. Applicator 520 is shown as having a convex presentation surface 516 similar to device 410 shown in FIG. 7. However, like other devices described above, presentation surface 516 may have another shape, such as concave or planar. Similarly, although first and second one-way valves 524, 526 are shown as being a ball-type valve and a duck-bill valve, respectively, these valves may be of another type, as discussed above in connection with device 10 of FIGS. 1A–C.

Piston pump 512 may include a piston tube 528, a piston 530, an actuator 532, and a linkage 534 connecting the actuator to the piston. Piston tube 528 defines a piston chamber 536 that contains piston 530 and may be located substantially at the bottom of reservoir 538 so that it may be filled with liquid by gravity when necessary and device 510 is in the upright orientation shown. In addition, this location will typically result in relatively little unusable liquid 514, i.e., liquid that would remain when its depth is too small to fill piston chamber 536. In this connection, piston tube 528 may be provided with at least one vent 540 that allows any air bubbles trapped within piston chamber 536 to exit into reservoir 538. Optionally, piston tube 528 may curve upwardly as shown and vent 540 may be located proximate piston 530 when the piston is in its first position 542 so that the vent is substantially at the highest point of piston chamber 536 to enhance the venting of air bubbles that may be trapped in the piston chamber. A second vent (not shown) may be provided in piston tube 528 on the backside of piston 530 when the piston is in first position 542 to allow liquid 514 behind the piston to flow back into reservoir 538 when piston is moved from a second position 544 back to the first position. Piston tube 528 may also include a third one-way valve 546, e.g., duckbill or other type one-way valve, that allows liquid 514 to be drawn into piston chamber 536 as piston 530 is moved from second position 544 to first position 542. Piston tube 528 may be made of any suitable material, such as plastic or metal, among others.

Piston 530 is slidable within piston chamber 536 and preferably forms a fluid seal around its outer periphery with piston tube 528. Piston 530 may be made of any suitable material, such as rubber or plastic. Those skilled in the art will appreciate the variety of configurations piston 530 may have, such that the piston need not be described in extensive detail herein.

Actuator 532 may include a slider 548 and a push button 550 fixedly attached to the slider. At least a portion of push button 550 is located on the outside of bottle 518 so that a user may push it to actuate piston pump 512. Slider 548 may be slidable engaged with bottle 518 in any suitable manner, such as by virtue of sidewall 552 of bottle being generally loosely clamped between push button 550 and the slider. Actuator 532 may be biased into a first position 554, e.g., by a spring (not shown) attached to, and extending between, bottle 518 and slider 548. The spring may be provided to hold actuator 532 in first position 554 and/or return the actuator to the first position after a user has moved the actuator toward second position 556 shown.

Push button 550 may be located in a recess 558 formed in bottle 518 to protect the push button from damage and/or from accidentally being pushed, thereby dispensing liquid 514 when this is not intended. Those skilled in the art will understand how slider 548 may be slidably engaged with bottle 518 such that a variety of ways need not be described herein. Push button 550 may include a stem 560 that extends through opening 562 and secures the push button to slider 548. A seal (not shown) may be provided in opening 562 between sidewall 552 and stem 560 to at least substantially fluidly seal reservoir 538 from the environment outside device 510. Alternatively, or additionally, an internal reservoir seal such as reservoir seal 450 of FIG. 7 may be provided to fluidly isolate reservoir 538 from the environment outside device 510. Push button 550 and slider 548 may be made of any suitable material, such as plastic or metal, among others.

Linkage 534 may be any linkage suitable for moving piston 530 in concert with actuator 532. For example, linkage 534 may be the generally semi-rigid rod shown. As used in this context, the term "semi-rigid" means the rod is rigid enough to carry a compressive load sufficiently large to move piston 530, but is flexible enough to accommodate the change in direction between slider 548 and the piston. In this connection, device 510 may further include at least one guide 564, e.g., a tube or other guide structure(s), for providing the lateral constraint necessary for the semi-rigid linkage 534 to carry the compressive load necessary to move piston 530 when actuator 532 is depressed. Of course, linkage 534 need not be a semi-rigid rod, but may be another linkage, such as a rigid member having a pin-type connection at each of its ends, among others. Those skilled in the art will understand that linkage 534 may have any of a variety of forms and how these forms may be implemented, such that each need not be described. Moreover, those skilled in the art will appreciate that actuator 532 may be a mechanism other than the push button 550/slider 548 arrangement shown. For example, actuator 532 may be comprised with an actuator wheel that enmeshes with a rack connected to, or incorporated in, linkage 534, or a lever arm having a toothed end that likewise enmeshes with a suitable rack, among others. Linkage and guide may be made of any suitable material, such as plastic, among others.

Device 510 may be used as follows. After uptake tube 522 and capillary tube 566 have been primed, a user may form droplet 568 on presentation surface 516 by actuating piston pump 512 by pushing push button 550 downward, i.e., generally toward the bottom of device 510, thereby moving actuator 532 from first position 554 to second position 556. As user pushes push button 550 downward, slider 548 moves downward, causing linkage 534 to move piston 530 from first position 542 to second position 544. Once piston 530 moves past vent 540, the pressure of liquid 514 within piston tube 528 and uptake tube 522 increases, thereby causing first one-way valve 524 to open and the liquid to be forced through capillary tube 566 to presentation surface 516 to form droplet 568.

Once actuator 532 and/or piston 530 have reached their respective travel limits or the user stops pushing push button 550, the pressure within piston tube 528 and uptake tube 522 will reduce, causing first one-way valve 524 to close, preventing droplet 568 from being sucked back into device 510. If a spring or other biasing means is provided for returning actuator 532 to first position 554, this spring will move the actuator and piston 530 back to their first positions 554 and 542, respectively, thereby causing a suction within uptake tube 522 and piston tube 528. If such spring is not provided, the user may push push button 550 upward to return actuator 532, and piston 530 to their respective first positions 554 and 542. This suction within uptake tube 522 and piston tube 528 causes third one-way valve 546 in the piston tube to open and cause liquid 514 to be drawn into the uptake tube from reservoir 538. Any negative pressure caused within bottle 518 by the pumping action of piston pump 512 will be substantially equalized by second one-way valve 526 opening when this negative pressure becomes great enough. Anytime after droplet 568 has been formed, the user may apply the droplet to an eye or other structure as discussed above in connection with FIGS. 1A–C.

Although only diaphragm, gear, and piston-type pumps have been described above, those skilled in the art will understand that a device of the present invention may include another type of pump, such as a peristaltic pump, e.g., a rotary peristaltic pump, among others. It is believed that those skilled in the art would understand the modifications necessary to implement one of these other pumps in lieu of the pumps shown. Therefore, it is believed that further examples showing other types of pumps is not necessary for those skilled in the art to appreciate the broad scope of the present invention.

Although the invention has been described and illustrated with respect to the exemplary embodiments thereof, it should be understood by those skilled in the art that the foregoing and various other changes, omissions and additions may be made therein and thereto, without parting from the spirit and scope of the present invention.

What is claimed is:

1. A device for dispensing a droplet of a liquid, comprising:
    a. a container for containing the liquid;
    b. an applicator secured to said container and having a presentation surface for presenting the droplet of the liquid, said presentation surface having a tilt angle $\alpha$ relative to a horizontal plane and a critical tilt angle $\alpha_{critical}$, such that when said tilt angle is 0°, said presentation surface faces upward; and
    c. a user-actuated mechanism for conveying the liquid to said presentation surface and forming the droplet on said presentation surface when said tilt angle is any angle from 0° to said critical tilt angle $\alpha_{critical}$.

2. A device according to claim 1, wherein said applicator includes at least one capillary passageway for communicating the liquid to said presentation surface when a user actuates said user-actuated mechanism so as to form the droplet on the presentation surface.

3. A device according to claim 2, wherein said applicator includes a plurality of capillary passageways for communicating the liquid to said presentation surface when a user actuates said user-actuated mechanism so as to form the droplet on the presentation surface.

4. A device according to claim 2, further comprising a one-way valve in fluid communication with said at least one capillary passageway for inhibiting the droplet from being sucked back into the device.

5. A device according to claim 1, wherein the droplet has a predetermined size and the device further comprises a metering apparatus for providing the droplet substantially in the predetermined size.

6. A device according to claim 5, wherein said container has a resiliently-deformable sidewall and said metering apparatus includes an internal stop for engaging said resiliently-deformable sidewall when a user squeezes said container.

7. A device according to claim 1, wherein said container has a resiliently-deformable sidewall and the device further includes an internal stop contained within said container for engaging said resiliently-deformable sidewall when a user squeezes said container.

8. A device according to claim 1, further comprising an uptake tube for communicating the liquid to said at least one capillary tube when a user actuates said user-actuated mechanism.

9. A device according to claim 8, wherein said uptake tube includes a central passageway and a one-way valve located within said central passageway for inhibiting the droplet from being sucked back into said reservoir.

10. A device according to claim 9, wherein said one-way valve is a duck-bill valve.

11. A device according to claim 1, wherein at least one of said container and said applicator has an opening and a one-way valve in fluid communication with said opening for equalizing the pressures inside and outside said container after a user actuates said user-actuated mechanism.

12. A device according to claim 11, wherein said one-way valve is a duck-bill valve.

13. A device according to claim 11, wherein said container has a resiliently-deformable sidewall and said user-actuated mechanism includes said resiliently-deformable sidewall.

14. A device according to claim 1, wherein said container has a resiliently-deformable sidewall and said user-actuated mechanism comprises said resiliently-deformable sidewall.

15. A device according to claim 1, wherein said device further comprises a reservoir contained in said container and said reservoir includes a collapsible sidewall.

16. A device according to claim 15, wherein said user-actuated mechanism collapses said collapsible sidewall when a user actuates said user-actuated mechanism.

17. A device according to claim 1, wherein the droplet has a predetermined size and said presentation surface includes at least one indicia visually indicating the predetermined size.

18. A device according to claim 17, wherein said at least one indicia is an annulus formed on said presentation surface.

19. An applicator securable to a container for forming a droplet of a liquid and presenting the droplet to a user, the container having an interior containing the liquid, comprising:

a. a body having an upper end and being adapted to be secured to the container;
b. a presentation surface formed on said upper end on which the droplet is formed when the applicator is in use; and
c. at least one capillary tube having a diameter of less than about 2 mm extending through said body for communicating the liquid between the interior of the container and said presentation surface when the applicator is in use.

20. An applicator according to claim 19, wherein said presentation surface is planar.

21. An applicator according to claim 19, wherein said presentation surface is concave.

22. An applicator according to claim 19, wherein said presentation surface is convex.

23. An applicator according to claim 19, wherein a plurality of capillary tubes extend through said body for communicating the liquid between the interior of the container and said presentation surface when the applicator is in use.

24. An applicator according to claim 19, wherein said body has a lower end and the applicator further comprises an uptake tube in fluid communication with said at least one capillary tube and engaged with said body at said lower end.

25. An applicator according to claim 24, wherein said uptake tube includes a one-way valve for inhibiting the droplet from being sucked from said presentation surface back into the container when the applicator is in use.

26. An applicator according to claim 19, wherein the applicator has an exterior with respect to the container when the applicator is secured to the container, said body further including a passageway extending between the exterior and the interior of the container when the applicator is secured to the container for equalizing the pressures inside and outside the container after the droplet has been formed on the presentation surface.

27. A system for applying a droplet to an eye, comprising:

a. a liquid agent for being applied to an eye; and
b. a device for forming a droplet of said liquid agent and presenting said droplet to the eye, comprising:
  i. a container containing said liquid agent;
  ii. an applicator secured to said container and having a presentation surface for presenting said droplet of said liquid agent, said presentation surface having a tilt angle $\alpha$ relative to a horizontal plane and a critical tilt angle $\alpha_{critical}$, such that when said tilt angle is 0°, said presentation surface faces upward; and
  iii. a user-actuated mechanism for conveying said liquid agent to said presentation surface and forming said droplet on said presentation surface when said tilt angle is any angle from 0° to said critical tilt angle $\alpha_{critical}$.

28. A system according to claim 27, wherein said liquid agent contains a medicament.

29. A system according to claim 27, wherein said liquid agent contains a moisturizer.

30. A system according to claim 27, wherein said applicator includes at least one capillary passageway for communicating the liquid to said presentation surface when a user actuates said user-actuated mechanism so as to form the droplet on the presentation surface.

31. A system according to claim 30, wherein said applicator includes a plurality of capillary passageways for communicating the liquid to said presentation surface when a user actuates said user-actuated mechanism so as to form the droplet on the presentation surface.

32. A system according to claim 30, further comprising a one-way valve in fluid communication with said at least one capillary passageway for inhibiting the droplet from being sucked back into the device.

33. A system according to claim 27, wherein the droplet has a predetermined size and the device further comprises a metering apparatus for providing the droplet substantially in the predetermined size.

34. A system according to claim 33, wherein said container has a resiliently-deformable sidewall and said metering apparatus includes an internal stop for engaging said resiliently-deformable sidewall when a user squeezes said container.

35. A system according to claim 27, wherein said container has a resiliently-deformable sidewall and the device further includes an internal stop contained within said container for engaging said resiliently-deformable sidewall when a user squeezes said container.

36. A system according to claim 27, further comprising an uptake tube for communicating the liquid to said at least one capillary tube when a user actuates said user-actuated mechanism.

37. A system according to claim 36, wherein said uptake tube includes a central passageway and a one-way valve located within said central passageway for inhibiting the droplet from being sucked back into said reservoir.

38. A system according to claim 37, wherein said one-way valve is a duck-bill valve.

39. A system according to claim 27, wherein at least one of said container and said applicator has an opening and a one-way valve in fluid communication with said opening for equalizing the pressures inside and outside said container after a user actuates said user-actuated mechanism.

40. A system according to claim 39, wherein said one-way valve is a duck-bill valve.

41. A system according to claim 39, wherein said container has a resiliently-deformable sidewall and said user-actuated mechanism includes said resiliently-deformable sidewall.

42. A system according to claim 27, wherein said container has a resiliently-deformable sidewall and said user-actuated mechanism comprises said resiliently-deformable sidewall.

43. A system according to claim 27, wherein said device further comprises a reservoir contained in said container and said reservoir includes a collapsible sidewall.

44. A system according to claim 43, wherein said user-actuated mechanism collapses said collapsible sidewall when a user actuates said user-actuated mechanism.

45. A method of applying a liquid agent to an eye with a device having a presentation surface having a tilt angle $\alpha$ relative to a horizontal plane and a critical tilt angle $\alpha_{critical}$, such that when the tilt angle is 0°, the presentation surface faces upward, comprising the steps of:

a. forming a droplet of the agent on the presentation surface when said tilt angle is any angle from 0° to said critical tilt angle $\alpha_{critical}$; and
b. contacting said droplet and the eye with one another when said tilt angle is any angle from 0° to said critical tilt angle $\alpha_{critical}$.

46. A method according to claim 45, wherein said eye is contained in a head and the step of contacting said droplet and the eye with one another includes tilting the head forward from an upright position.

* * * * *